United States Patent
Gotz et al.

(10) Patent No.: US 10,667,674 B2
(45) Date of Patent: Jun. 2, 2020

(54) MEDICAL INSTRUMENT WITH HANDLE

(71) Applicant: Scholly Fiberoptic GmbH, Denzlingen (DE)

(72) Inventors: Maximilian Gotz, Freiburg (DE); Rainer Wilczynski, Vorstetten (DE); Jurgen Gamer, Denzlingen (DE); Matthias Kuhn, Freiburg (DE)

(73) Assignee: SCHOLLY FIBEROPTIC GMBH, Denzlingen (DE)

( * ) Notice: Subject to any disclaimer, the term of this patent is extended or adjusted under 35 U.S.C. 154(b) by 478 days.

(21) Appl. No.: 15/067,614

(22) Filed: Mar. 11, 2016

(65) Prior Publication Data

US 2016/0296103 A1    Oct. 13, 2016

(30) Foreign Application Priority Data

Apr. 8, 2015  (DE) .................. 10 2015 004 546

(51) Int. Cl.
*A61B 1/00*    (2006.01)
*A61B 90/00*   (2016.01)

(52) U.S. Cl.
CPC ...... *A61B 1/00142* (2013.01); *A61B 1/00066* (2013.01); *A61B 2090/0813* (2016.02)

(58) Field of Classification Search
CPC ...... A61B 17/2909; A61B 2017/00367; A61B 2017/00371; A61B 2017/00376; A61B 2017/0038; A61B 2017/00384; A61B 2017/00389; A61B 2017/00393; A61B 2017/00017; A61B 2017/00398; A61B 2017/2912

USPC ....... 600/109, 110, 119, 121, 122, 131, 132, 600/146, 147, 148, 149, 150, 151, 152, 600/160

See application file for complete search history.

(56) References Cited

U.S. PATENT DOCUMENTS

| | | | | |
|---|---|---|---|---|
| 5,354,291 A * | 10/1994 | Bales | ......... | A61M 1/0064 604/22 |
| 5,830,214 A * | 11/1998 | Flom | ......... | A61B 18/1482 606/41 |
| 5,871,493 A * | 2/1999 | Sjostrom | ......... | A61B 17/162 604/22 |
| 6,500,169 B1 * | 12/2002 | Deng | ......... | A61B 17/00 606/1 |
| 6,561,971 B1 * | 5/2003 | Akiba | ......... | A61B 1/00188 600/131 |

(Continued)

FOREIGN PATENT DOCUMENTS

DE    102016214530    2/2018
JP    2006255107      9/2006

*Primary Examiner* — Timothy J Neal
*Assistant Examiner* — William B Chou
(74) *Attorney, Agent, or Firm* — Volpe and Koenig, P.C.

(57) ABSTRACT

A medical instrument (1) designed in particular as an endoscope (2) has a main body (3) and, formed on the main body (3), an electrical and/or electronic switching device (4) with at least one button (5) for actuating the switching device (4) and the medical instrument (1). The switching device (4) is provided on its outside (6) with a cover (7), which is integrally bonded to the main body (3) of the medical instrument (1) in order to produce a tight connection. Provision is further made that the cover (7) has at least one outwardly directed bulge (8), on which the at least one button (5) of the switching device (4) is formed.

20 Claims, 1 Drawing Sheet

(56) References Cited

U.S. PATENT DOCUMENTS

| | | | | |
|---|---|---|---|---|
| 7,156,844 B2* | 1/2007 | Reschke | ............ | A61B 18/1402 |
| | | | | 606/41 |
| 9,931,118 B2* | 4/2018 | Shelton, IV | ....... | A61B 17/2909 |
| 2001/0049524 A1* | 12/2001 | Morgan | ............... | A61B 18/148 |
| | | | | 606/50 |
| 2002/0049464 A1* | 4/2002 | Donofrio | ......... | A61B 17/32006 |
| | | | | 606/169 |
| 2002/0095088 A1* | 7/2002 | Jordfald | .................. | A61B 8/12 |
| | | | | 600/462 |
| 2003/0065321 A1* | 4/2003 | Carmel | .............. | A61B 18/1402 |
| | | | | 606/41 |
| 2003/0176778 A1* | 9/2003 | Messing | ................ | A61B 18/00 |
| | | | | 600/374 |
| 2007/0142824 A1 | 6/2007 | Devengenzo et al. | | |
| 2007/0219409 A1 | 9/2007 | Shimizu et al. | | |
| 2010/0069940 A1* | 3/2010 | Miller | ............. | A61B 17/32006 |
| | | | | 606/169 |
| 2011/0112518 A1* | 5/2011 | Stanton | .................. | A61B 17/00 |
| | | | | 606/1 |
| 2014/0100424 A1 | 4/2014 | Hoshino | | |
| 2014/0221749 A1* | 8/2014 | Grant | ................ | A61B 1/00183 |
| | | | | 600/112 |
| 2014/0288536 A1* | 9/2014 | Le | ...................... | A61B 17/1624 |
| | | | | 606/1 |
| 2014/0303611 A1* | 10/2014 | Shadduck | ........... | A61B 18/148 |
| | | | | 606/33 |
| 2015/0144514 A1* | 5/2015 | Brennan | ............ | A61F 9/00736 |
| | | | | 206/363 |
| 2015/0148615 A1* | 5/2015 | Brennan | ............ | A61F 9/00736 |
| | | | | 600/249 |

* cited by examiner

MEDICAL INSTRUMENT WITH HANDLE

INCORPORATION BY REFERENCE

The following documents are incorporated herein by reference as if fully set forth: German Patent Application no. DE 102015004546.6, filed Apr. 8, 2015.

BACKGROUND

The invention relates to a medical instrument, in particular an endoscope, with a main body and, formed on the main body, an electrical and/or electronic switching device with at least one button for actuating the switching device and the medical instrument.

Instruments of this kind are known, for example, from endoscopes and other electrically operated medical instruments. The switching device of such a medical instrument serves to switch a function of this instrument on and off during the use of the medical instrument.

Since such medical instruments are in most cases very expensive, there is a need to ensure that they are not disposed of after just one use but instead can be reconditioned for further use. However, due to the strict hygiene requirements in medical interventions in which such medical instruments are used, the medical instruments have to be sterilized after use. This can be done, for example, by autoclaving or by a treatment with disinfecting chemical substances.

Since the medical instrument is exposed to very aggressive conditions during this sterilizing process, it is necessary, however, that the electric and/or electronic switching device arranged in or on the medical instrument, and in particular in or on the main body, is protected from being damaged or destroyed during the reconditioning of the medical instrument.

SUMMARY

The object of the invention is therefore to make available a medical instrument of the type defined at the outset, in which the switching device formed on the main body of the medical instrument can be reliably protected from being damaged or destroyed during reconditioning of the medical instrument.

This object is achieved by a medical instrument having one or more features of the invention, and in particular in a medical instrument of the type described at the outset, by the fact that the switching device has on its outside a cover, which is integrally bonded to the main body of the medical instrument in order to produce a tight connection, and that the cover has at least one outwardly directed bulge, on which the at least one button of the switching device is formed.

By virtue of the tight and integrally bonded connection between the cover of the switching device and the main body of the medical instrument, entry of chemical sterilization substances into the switching device can be very largely or even completely avoided and/or it is possible to suppress a damaging effect of the reconditioning process of the medical instrument on the switching device, such that there is no risk of the switching device being damaged or totally destroyed by the process of reconditioning of the medical instrument.

In a particularly expedient embodiment of the medical instrument according to the invention, provision can be made that the cover is made of a sheet metal, in particular a corrosion-resistant material, for example stainless steel. In addition, it may be expedient if the sheet metal is provided with a coating. This can promote a tight, integrally bonded connection of the cover to the main body of the medical appliance.

It is also possible that the cover, along its edge, is integrally bonded in a tight connection to the main body of the medical instrument.

On the one hand, a robust coverage of the switching device can be obtained in this way, such that the latter can withstand very aggressive or extremely aggressive conditions, and, on the other hand, the integrally bonded and tight connection between the cover and the main body of the medical instrument makes it possible to ensure that substances used for disinfecting and sterilizing the medical instrument cannot get into the switching device.

With the outwardly directed bulge of the cover on which the at least one button of the switching device is formed, the cover is able not only to protect the switching device arranged under it but also to assume a further function, namely that of providing an interface between the switching device and a user, which interface is easy for a user to feel by way of the bulge of the cover in the area of the button.

For operating the switching device of the medical instrument, it may be advantageous if the at least one bulge for actuating the switching device is designed such that it can be pressed in resiliently and reversibly. In order to actuate the switching device, it is then possible to move the bulge, for example by pressing a finger against it, from its outwardly curved position to a depressed or indented position, which corresponds to a switching position. It may be particularly expedient if the bulge has a defined pressure point. For example, in the case of a body that can be moved elastically counter to a restoring force, a pressure point can be characterized by the fact that, when the pressure point is exceeded, the restoring force suddenly decreases, but it then increases again, or at least does not decrease, as the action continues.

It is thus possible that a performed actuation of the switching device can be perceived haptically by a user, since the resistance of the bulge, against a user who is pressing it in, is abruptly reduced or completely suppressed when the pressure point of the bulge is reached.

The bulge can therefore be of an elastic configuration and can apply a restoring force against a pressing-in of the bulge.

It may be expedient if the main body is made of a metallic material or is at least metallized in a connection area between the cover and the main body. Alternatively or additionally, provision can also be made that the main body has a metallic or metallized surface. This is particularly so when the main body is actually made of a non-metallic material.

It is possible in this way for a metallic or metallized cover to be connected in an integrally bonded and therefore tight manner to the metallic or metallized main body. A further advantage of the use of a metallic material is that, by virtue of its inherent dimensional stability, it can be configured with a form that defines a pressure point.

Provision can be made that the integrally bonded connection between the cover and the main body is produced by gluing, soldering or welding, in particular by laser welding.

It may be particularly advantageous if the medical instrument can be thermally and/or chemically reconditioned, in particular sterilized, preferably autoclaved.

With respect to the operation of the switching device, a configuration of the medical instrument that is particularly resistant to wear can be obtained if the switching device has an electric switch which is separated from the cover by an air gap and which is configured for contactless switching.

Provision can be made that the contactless switching is effected by a change of position and/or shape of the inside of the cover, in particular by optical, magnetic or electrical interaction. The air gap can in this case be formed between an inner face of the cover, directed toward the switch, and the cover.

A particularly simple configuration of the medical instrument can also be obtained if the at least one button on the cover is formed on the medical instrument in such a way as to be able to be touched directly from the outside.

Thus, it is not necessary for any movable element, for example a plunger or the like, to be arranged outside of the closure of the switching device defined by the cover in order to be able to actuate the switching device. Movable elements of this kind generally always have gaps or cracks in which contaminants are able to settle which are disadvantageous for the use of the medical instrument in the medical sector and which make cleaning, disinfecting and sterilizing of the medical instrument difficult.

To be able to reliably avoid a contamination of the medical instrument, its main body and/or the switching device, even during the use of the medical instrument, it may be expedient if the main body and/or the switching device are closed off tightly by the cover of the switching device, in particular so as to be gas-tight, vapor-tight and/or liquid-tight.

For particularly simple production of the switching device and of its cover, it is expedient if a bulge with a button is formed on the cover. In medical instruments in which more than just one function has to be switched on during use, it may be expedient if two or three or more buttons are formed on the cover. Preferably, each of the buttons can be arranged on its own bulge of the cover, and the actuation and/or control of a function of the medical instrument can be assigned to each of the buttons present on the cover.

In a further embodiment of the medical instrument, provision can be made that the cover has a depression in which the at least one button or several buttons are arranged. However, it is also possible that the cover has, for each of the buttons present on the cover, a respective depression in which one of the buttons present is arranged.

It may be expedient if a height of the at least one bulge of the cover, on which the at least one button is formed, is less than a depth of the depression of the cover. In this way, it is possible that the bulge with the button is recessed in the depression of the cover. In another embodiment of the medical instrument, provision can be made that a height of the at least one bulge of the cover, on which the at least one button is formed, is at most as great as the depth of the depression of the cover. In this way, a cover with its bulge is provided that does not protrude from the depression of the cover.

In a third embodiment of the medical instrument, provision can additionally be made that the at least one bulge protrudes from the depression in which it is arranged.

It will be noted at this point that, in a further embodiment of the medical instrument, provision can also be made that it has a switching device with a cover on which several bulges with buttons are provided, of which one is arranged recessed in a depression, one is arranged recessed in a depression and not quite protruding beyond the depression, and another one is arranged in a depression of the cover in such a way that the bulge protrudes from the depression. Other combinations of these cases can also be formed.

The inside of the at least one bulge can concavely delimit a hollow space.

The medical instrument can have a particularly simple structure if the above-described cover is mounted from the outside onto the main body. The cover can be mounted onto the outside of the main body. Thus, a simple connection site between the cover and the main body can be created in which undercuts, joins and/or grooves between the cover and the main body can be reduced or even avoided. A medical instrument is thus created that can be conditioned, cleaned, disinfected and/or sterilized in a particularly simple and reliable manner. When undercuts, joins and/or grooves are present, there is a risk of dirt collecting there, and this dirt can only be removed at great effort, if indeed at all, when conditioning, cleaning, disinfecting or also sterilizing the medical instrument.

BRIEF DESCRIPTION OF THE DRAWINGS

Illustrative embodiments of the invention are described in detail below with reference to the drawing, in which the depictions are highly schematic in part and in which.

DETAILED DESCRIPTION OF THE PREFERRED EMBODIMENTS

Figure 1:
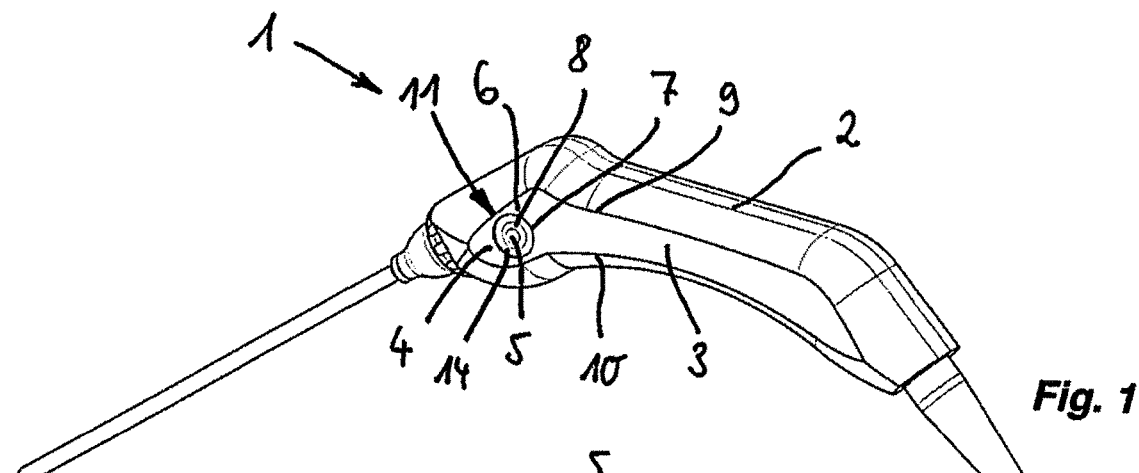
FIG. 1 shows a perspective view of a medical instrument according to the invention in the form of an endoscope, wherein a switching device according to the invention can be seen on a side face of the endoscope directed toward the observer.

A medical instrument designated overall by 1 is designed as an endoscope 2 in FIG. 1. The medical instrument 1 has a main body 3 and, formed on the main body 3, an electrical and/or electronic switching device 4.

At least one button 5 is provided on the switching device 4 for the purpose of actuating the switching device 4 and the medical instrument 1.

According to the figures, the switching device 4 has on an outside 6 a cover 7, which is integrally bonded to the main body 3 of the medical instrument 1 in order to produce a tight connection. This cover 7 is mounted from the outside onto the main body 3.

All of the figures additionally show that the cover 7 has at least one outwardly directed bulge 8, on which the at least one button 5 of the switching device 4 is formed.

The cover 7 shown in the figures is made from a sheet metal comprised of a corrosion-resistant material, for example stainless steel. Along its edge 9, the cover 7 is integrally bonded in a tight connection to the main body 3 of the medical instrument 1.

In order to make available a reliable and simple connection between the main body 3 and the cover 7 made of the sheet metal, the cover 7, more precisely the sheet metal, can additionally be provided with a coating.

Figure 3:
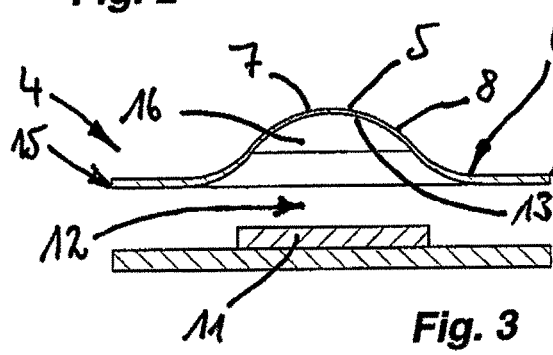
FIG. 3 shows a schematic cross-sectional view of a switching device according to the invention in the unactuated position, revealing the cover with a bulge, on which the button of the switching device can be seen, and, below the bulge, a switch of the switching device.
Figure 4:
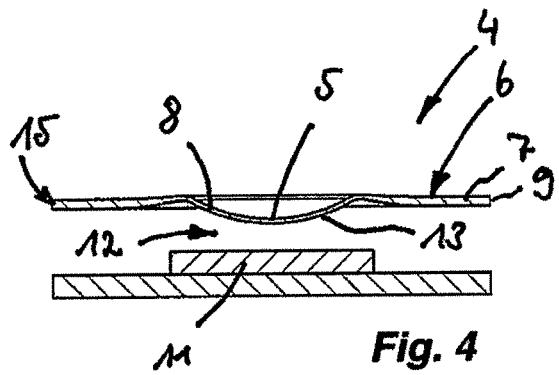
FIG. 4 shows a further cross-sectional view of the switching device shown in FIG. 3, wherein the switching device is shown in the actuated position, i.e. with the bulge pressed inward.

The at least one bulge 8 is designed to be able to be pressed in resiliently and reversibly in order to actuate the switching device 4. This is shown in FIGS. 3 and 4 in particular.

The bulge 8 has a defined pressure point, by which a performed actuation of the switching device 4 can be perceived haptically by a user. In one embodiment of the medical instrument 1, the main body 3 is made of a metallic material. In another embodiment of the medical instrument 1, provision is made that the main body 3 is metallized and/or has a metallic or metallized surface 10 at least in a connection area between the cover 7 of the switching device 4 and the main body 3. FIG. 3 shows the cover 7 before the pressure point is reached, while FIG. 4 shows it after a deformation beyond the pressure point. After the pressure is removed from the cover 7 in FIG. 4, the cover 7 snaps back into the starting position according to FIG. 3.

The integrally bonded connection between the cover 7 and the main body 3 of the medical instrument 1 is preferably produced by gluing, soldering or welding, in particular by laser welding.

The choice of the connection method is, on the one hand, dependent on the material of the cover 7 and, on the other hand, dependent on the material of the main body 3 in the connection area between the cover 7 and the main body 3.

The medical instrument 1 is designed in such a way that it can be thermally and/or chemically reconditioned, in particular sterilized and preferably autoclaved.

According to FIGS. 3 and 4, the switching device 4 has an electric switch 11 which is separated from the cover 7 by an air gap 12 between an inner face 13 of the cover 7, directed toward the switch 11, and the cover 7.

The electric switch 11 is configured for contactless switching, preferably by a change of a position and/or shape of the inner face 13 of the cover 7. Depending on the configuration of the switching device 4, this can be done by optical, magnetic and/or electrical interaction.

All the figures show that the at least one button 5 on the cover 7 is formed on the medical instrument 1 in such a way as to be able to be touched directly from the outside.

The main body 3 and/or the switching device 4 are closed tightly by the cover 7 of the switching device 4, in particular so as to be gas-tight, vapor-tight and/or liquid-tight. In other words, the main body 3 and/or the switching device 4 can be sealed off tightly and hermetically with the aid of the cover 7.

Figure 2:
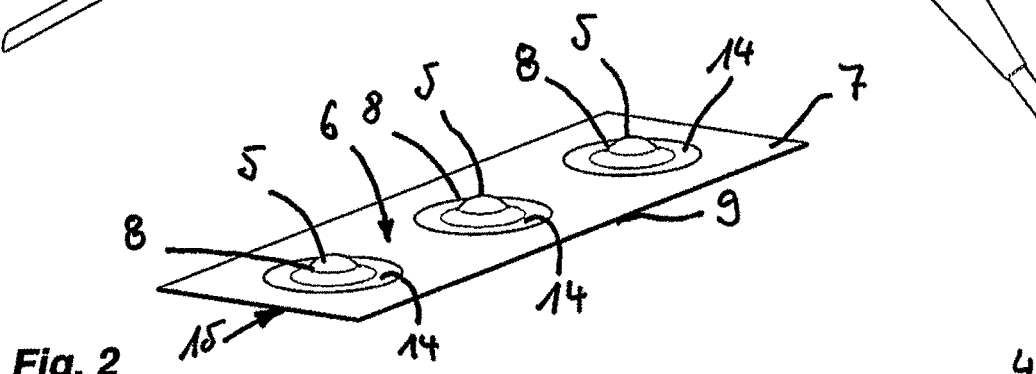
FIG. 2 shows a perspective top view of a cover, according to the invention, of a switching device on which three bulges in total are formed, each of them with a button.

According to FIG. 2, three buttons 5 are formed on the cover 7, wherein each of the buttons 5 is arranged on a respective bulge 8 of the cover 7.

The actuation and/or control of a function of the medical instrument 1 is assigned to each of the buttons 5 present on the cover 7.

According to FIGS. 1 to 7, the cover 7 has at least one depression 14 in which the buttons 5 present on the cover 7 are arranged. According to FIG. 2, the cover 7 for each of the buttons present on the cover 7 in each case has a depression 14 in which one of the buttons 5 present is arranged.

Figure 5:
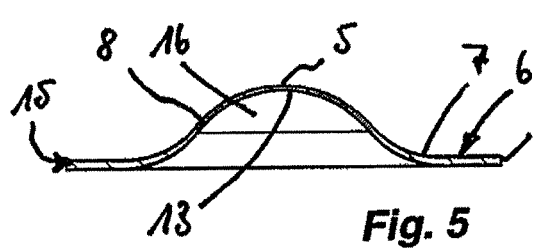
FIG. 5 shows a cross-sectional view of the cover shown in FIGS. 3 and 4, revealing that the bulge is arranged above a base plane of the cover.

According to FIG. 5, the bulge 8 of the cover 7 is arranged on the cover 7 such that it is positioned on a main plane 15 of the cover 7.

Figure 6:
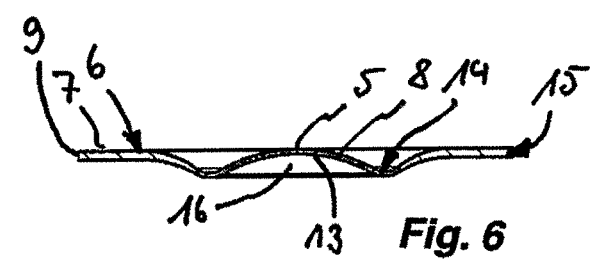
FIG. 6 shows a cross-sectional view of a further cover of a switching device, revealing that the bulge on which the button of the switching device is formed is arranged in a depression provided in the cover, wherein a height of the bulge corresponds to a depth of the depression.
Figure 7:
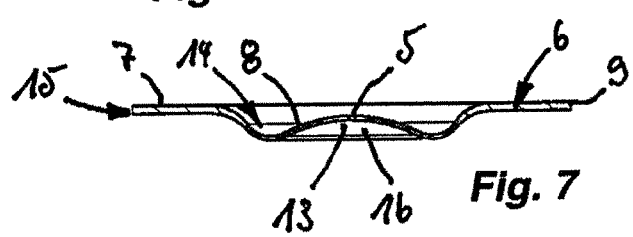
FIG. 7 shows a cross-sectional view of a further cover of a switching device according to the invention, revealing that the bulge on which the button of the switching device is formed is arranged recessed in a depression of the cover, and wherein a height of the bulge is less than a depth of the depression.

According to the illustrative embodiments of the cover 7 shown in FIGS. 6 and 7, the bulge 8 on which the at least one button 5 of the switching device 4 is formed is in each case arranged inside a depression 14 of the cover 7.

According to FIG. 6, the height of the bulge 8 shown there corresponds to the depth of the depression, such that a convex top face of the bulge 8 bears tangentially from underneath on the imaginary main plane 15 of the cover 7.

In the illustrative embodiment shown in FIG. 7, the height of the bulge 8 arranged there inside the depression 14 is less than the depth of the depression 14, such that the top face of the bulge 8 is arranged at a distance from the imagined base plane 15 of the cover 7 of the switching device 4.

A common feature of all of the bulges shown in the figures is that they concavely delimit a hollow space 16 on the inside.

The medical instrument 1 designed in particular as an endoscope 2 has the main body 3 and the electric and/or electronic switching device 4 formed on the main body 3, with at least one button 5 for actuating the switching device 4 and the medical instrument 1. On its outside 6, the switching device 4 is provided with the cover 7 which is integrally bonded to the main body 3 of the medical instrument 1 to produce a tight connection. Provision is further made that the cover 7 has the at least one outwardly directed bulge 8 on which the at least one button 5 of the switching device 4 is formed.

LIST OF REFERENCE SIGNS

1 medical instrument
2 endoscope
3 main body
4 switching device
5 button
6 outside
7 cover
8 bulge
9 edge of the cover
10 metallized surface
11 switch
12 air gap
13 inner face of 7
14 depression
15 base plane
16 hollow space

The invention claimed is:

1. A medical instrument (1), comprising a main body (3) and, formed on the main body (3), at least one of an electrical or electronic switching device (4) with at least one button (5) for actuating the switching device (4) and the medical instrument (1), a cover (7) located on an outside of the switching device (4), the cover (7) being integrally bonded along an edge (9) thereof to the main body (3) of the medical instrument (1) in order to produce a sealed connection, the cover (7) includes at least one integrally formed outwardly directed bulge (8), on which the at least one button (5) of the switching device (4) is integrally formed, and the switching device (4) has an electric switch (11) which is separated from the cover (7) by an air gap (12), and is configured for contactless switching.

2. The medical instrument (1) as claimed in claim 1, wherein the cover (7) is made of sheet metal, and the cover (7) has a reduced thickness in a central region of the at least one integrally formed outwardly directed bulge (8) compared to a radially outer region of the at least one integrally formed outwardly directed bulge (8).

3. The medical instrument (1) as claimed in claim 2, wherein the sheet metal is a corrosion-resistant material.

4. The medical instrument (1) as claimed in claim 1, wherein the sheet metal is provided with a coating.

5. The medical instrument (1) as claimed in claim 1, wherein the at least one integrally formed outwardly directed bulge is formed of a flexible material.

6. The medical instrument (1) as claimed in claim 5, wherein the integrally bonded connection between the cover (7) and the main body (3) is produced by gluing, soldering, welding, or laser welding.

7. The medical instrument (1) as claimed in claim 1, wherein the at least one integrally formed outwardly directed bulge (8) is resiliently and reversibly pressed in for actuating the switching device.

8. The medical instrument (1) as claimed in claim 1, wherein the at least one integrally formed outwardly directed bulge (8) has a defined pressure point.

9. The medical instrument (1) as claimed in claim 1, wherein the main body (3) is made of a metallic material, is metallized at least in a connection area between the cover (7) and the main body (3), or has a metallic or metallized surface (10).

10. The medical instrument (1) as claimed in claim 1, wherein the medical instrument (1) is at least one of thermally or chemically reconditionable.

11. The medical instrument (1) as claimed in claim 1, wherein the air gap (12) is located between an inner face (13) of the cover (7), facing toward a switch (11) of the switching device (4), and the cover (7), and the contactless switching takes place by a change of at least one of a position or shape of the inner face (13) of the cover (7), by at least one of an optical, magnetic, or electrical interaction.

12. The medical instrument (1) as claimed in claim 1, wherein the at least one button (5) on the cover (7) is formed on the medical instrument (1) to be touchable directly from an outside.

13. The medical instrument (1) as claimed in claim 1, wherein at least one of the main body (3) or the switching device (4) are closed by the cover (7) of the switching device (4) in at least one of a gas-tight, vapor-tight, or liquid-tight manner.

14. The medical instrument (1) as claimed in claim 1, wherein two or three or more of the buttons (5) are formed on the cover (7), and each of the buttons (5) is arranged on separate ones of the integrally formed outwardly directed bulges (8) of the cover (7), and at least one of the actuation or control of a function of the medical instrument (1) is assigned to each of the buttons (5) present on the cover (7).

15. The medical instrument (1) as claimed in claim 1, wherein the cover (7) has a depression (14) in which the one or more buttons (5) present are arranged, and the cover (7) has, for each of the buttons (5) present on the cover (7), a respective depression (14), in which one of the buttons (5) present is respectively arranged.

16. The medical instrument (1) as claimed in claim 15, wherein a height of the at least one integrally formed outwardly directed bulge (8) of the cover (7), on which the at least one button (5) is formed, is less than a depth or at most as great as a depth of the depression(s) (14) of the cover, or the at least one integrally formed outwardly directed bulge (8) protrudes from the depression (14).

17. The medical instrument (1) as claimed in claim 1, wherein an inside of the at least one integrally formed outwardly directed bulge (8) concavely delimits a hollow space (16).

18. The medical instrument (1) as claimed in claim 1, wherein the cover (7) is mounted from outside onto the main body (3).

19. The medical instrument (1) as claimed in claim 1, wherein the medical instrument is an endoscope.

20. The medical instrument (1) as claimed in claim 1, wherein the air gap (12) is partially defined between a bottom surface of the at least one button (5) and an upper surface of the electric switch (11).

* * * * *